United States Patent [19]

Griffith et al.

[11] Patent Number: 4,769,466
[45] Date of Patent: Sep. 6, 1988

[54] 2-AMINOACETAMIDE PYRIDINYL DERIVATIVES

[75] Inventors: Ronald C. Griffith, Pittsford; James J. Napier, Rochester, both of N.Y.

[73] Assignee: Pennwalt Corporation, Philadelphia, Pa.

[21] Appl. No.: 11,983

[22] Filed: Feb. 6, 1987

[51] Int. Cl.$^4$ ............................................. C07D 213/56
[52] U.S. Cl. ................................. 546/337; 546/265; 546/193; 546/194; 546/275; 544/124
[58] Field of Search ......................................... 546/337

[56] References Cited

U.S. PATENT DOCUMENTS 4,500,714  2/1985  Honda et al. ....................... 546/337

FOREIGN PATENT DOCUMENTS 955508  1/1957  Fed. Rep. of Germany ...... 546/337
343388  2/1960  Switzerland ........................ 546/337

OTHER PUBLICATIONS

CA 64,14162f.
CA 73,25044n.
CA 77,19586g.
CA 85,5705y.
CA 96,19744z.

Primary Examiner—M. C. Lee
Assistant Examiner—J. Richter

[57] ABSTRACT

Compounds are provided of the following general structure:

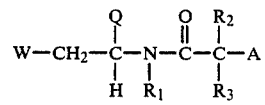

wherein $R_1$, $R_2$ and $R_3$ are independently selected from hydrogen or methyl; A is amino, $C_1$-$C_4$ monoalkylamino, $C_2$-$C_8$ dialkylamino, 1-pyrrolidinyl, 1-piperidinyl, 4-morpholinyl or cyclopropylamino; and where W and Q are independently selected from 2-pyridinyl, 3-pyridinyl or 4-pyridinyl or phenyl, provided W and Q are not both phenyl.

11 Claims, No Drawings

2-AMINOACETAMIDE PYRIDINYL DERIVATIVES

SUMMARY OF THE INVENTION

Novel substituted 2-aminoacetamide derivatives have been prepared and found to possess useful sedative, analgesic and antiepileptic activity.

GENERAL DESCRIPTION

This invention relates to novel 2-aminoacetamide compounds of the following general structure (1):

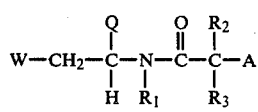

wherein $R_1$, $R_2$ and $R_3$ are independently selected from hydrogen or methyl; A is amino, $C_1$-$C_4$ monoalkylamino, $C_2$-$C_8$ dialkylamino, 1-pyrrolidinyl, 1-piperidinyl, 4-morpholinyl or cyclopropylamino; and where W and Q are independently selected from 2-pyridinyl, 3-pyridinyl or 4-pyridinyl or phenyl, provided W and Q are not both phenyl.

This invention also relates to diastereomeric and optically resolved forms, and to pharmaceutically acceptable acid addition salts of the compounds of general formula (1).

Compounds of this invention possess useful pharmaceutical properties. In particular they possess sedative, analgesic and antiepileptic properties. Especially useful compounds are those in which $R_1$, $R_2$ and $R_3$ are hydrogen and A is amino.

DETAILED DESCRIPTION

The 2-aminoacetamides of general formula (1) as described fully above are conveniently prepared by suitable amide bond forming reactions from the corresponding amine intermediates of general formula (2):

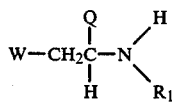

where the letters Q, $R_1$ and W are as defined above. Most of the amines of general formula (2) are known compounds and may be conveniently prepared by suitable modifications of the reported procedures. Some of the amines (2) are not known, but are prepared by similar procedures. The preparation of the amines of general formula (2) is described in the "Preparation of Intermediates" Section.

Many amide bond forming reactions may in principle be utilized for the conversion of the amines of general formula (2) to the amides of general formula (1). Two procedures which represent the preferred methods for this conversion are designated Method A and Method B.

Method A consists of direct coupling of commercially available suitably protected aminoacid derivatives of formula (3):

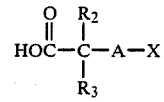

where $R_2$ and $R_3$ are as described above, A is amino or $C_1$-$C_4$ monoalkylamino and where X is an urethane protecting group preferably benzyloxycarbonyl (CBZ) or t-butyloxycarbonyl (BOC), with an amine of general formula (2), in an inert solvent in the presence of a coupling reagent such as dicyclohexylcarbodiimide with or without 1-hydroxybenzotriazole or other additives to provide coupled products of general formula (4):

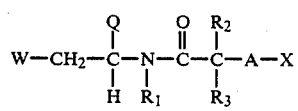

The protecting groups X, are then readily removed by either catalytic hydrogenation for the CBZ group or treatment with an acid such as trifluoroacetic or hydrochloric acid for the BOC group to provide the compounds of general formula (1). This procedure is especially useful for the preparation of compounds of formula (1) where A is amino.

Method B consists of reacting an amine of general formula (2) with an activated two carbon acid derivative which contains a leaving group alpha to the carbonyl, such as chloroacetyl chloride, in the presence of an acid acceptor, such as triethylamine, to produce the corresponding 2-chloroacetamide derivative of general formula (5):

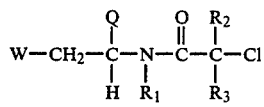

Such an intermediate can be directly reacted with ammonia or amines such as $C_1$-$C_4$ monoalkylamines, $C_2$-$C_8$ dialkylamines, cyclopropylamine, pyrrolidine, piperidine or morpholine in a solvent such as a lower alkanol, for example methanol or ethanol, or a chlorinated solvent, for example chloroform or methylene chloride or mixtures thereof to provide the corresponding compounds of general formula (1) where A=amino, $C_1$-$C_4$ monoalkylamino, $C_2$-$C_8$ dialkylamino, cyclopropylamino, 1-pyrrolidinyl, 1-piperidinyl or 4-morpholinyl.

The compounds of general formula (1) possess asymmetric centers, and therefore geometric and optical isomers are possible. Such compounds are conveniently prepared from optically active amines of formula (2) and/or from optically active aminoacid intermediates of formula (3) by the methods described above.

The compounds of general formula (1) are basic compounds and may be used as such or pharmaceutically acceptable acid addition salts may be prepared by treatment with various inorganic or organic acids, such as hydrochloric, hydrobromic, sulfuric, phosphoric, acetic, lactic, succinic, fumaric, malic, maleic, tartaric, citric, benzoic, methanesulfonic or carbonic acids.

The compounds of general formula (1) possess useful pharmaceutical properties. In particular they possess useful antiepileptic and sedative properties and in some cases they possess analgesic properties. These activities were assessed by standard methods. Antiepileptic activity was measured by assessing a compound's ability to prevent the hind limb tonic extension component of the seizure in groups of mice induced by maximal electroshock after oral or intraperitoneal administration according to the procedures of the Epilepsy Branch, NINCDS as published by R. J. Porter, et al., *Cleve. Clin. Quarterly* 1984, 51. 293, and compared to the standard agents dilantin and phenobarbital. Activities in the range of 10–400 m/k after oral administration in this assay system were obtained. Sedative activity was assessed by behavioral observation in groups of mice and analgesic activity was assessed by measuring the ability of a compound to prevent para-benzoquinone (PBQ) induced writhing in mice by standard literature procedures. Selected compounds exhibited activity in the range of 30–600 m/k in these assays.

The following non-limiting illustrations and examples are provided to exemplify the preparation of the intermediate amines of formula (2) and their conversion to the novel compounds of general formula (1).

PREPARATION OF INTERMEDIATES

Illustration 1

Preparation of 1-(2-Pyridinyl)-2-phenylethylamine dihydrochloride

This compound was prepared by suitable modification of the procedures described by Niemers and Hiltman, *Synthesis*, 1976, 593 as follows. To a solution of 1-(2-pyridinyl)-2-phenylethanone (Case and Buttle, *J. Org. Chem.*, 1961, 26, 4415) (49.05 g, 0.249 mol) in 95% ethanol (400 ml) was added a solution of hydroxylamine hydrochloride (51.91 g, 0.747 mol) in 10% sodium hydroxide (200 ml). The solution was heated to reflux under nitrogen for 1.25 hours, and stirred at room temperature for 48 hours. The majority of the solvent was removed and the residue was added to water (500 ml). The aqueous solution was extracted with ether (1×1000 ml, and 3×250 ml). The combined ether extracts were washed with saturated NaCl and dried over MgSO$_4$. Removal of solvent gave 55.61 g of the crude product as a brown solid. The above solid was dissolved in cyclohexane (400 ml) and ether (500 ml) and filtered while hot. The filtrate was concentrated to a volume of 500 ml and cooled to room temperature. The solid which formed was isolated by filtration to yield 20.77 g of 1-(2-pyridinyl)-2-phenylethanone oxime; mp 151°–153° C.

To a solution of the above oxime (19.00 g, 0.090 mol) in methanol (385 ml) and 10% hydrochloric acid (90 ml) was added 10% palladium on carbon (3.5 g). The mixture was shaken on a Parr apparatus under an atmosphere of hydrogen for 23 hours. The majority of the solvent was removed and the residue was dissolved in water (250 ml). This solution was basified to a pH of 11 with 50% sodium hydroxide and extracted with chloroform (3×250 ml). The combined chloroform extracts were washed with saturated NaCl (250 ml) and dried over MgSO$_4$. Removal of solvent gave 16.93 g of crude amine as a dark oil. The above oil was dissolved in absolute ethanol (250 ml) and treated with gaseous HCl. Upon standing a white solid crystallized which was collected by filtration to give 18.36 g of 1-(2-pyridinyl)-2-phenylethylamine dihydrochloride; mp 243°–245° C.

Illustration 2

Preparation of 1-(3-Pyridinyl)-2-phenylethylamine dihydrochloride

N-(Trimethylsilyl)pyridine-3-carboxaldimine was prepared in situ by the method of Hart, Kanai, Thomas and Yang *J. Org. Chem.*, 1983, 48, 289 as follows. To a solution of hexamethyldisilazine (106 ml, 0.50 mol) in tetrahydrofuran (500 ml) at 0° C. under nitrogen was added a solution of n-butyllithium (238 ml of 2.1 m hexane solution, 0.50 mol) at such a rate that the temperature of the reaction did not exceed 12° C. The solution was stirred with cooling for an additional hour. The above solution was added dropwise to an ice cooled solution of pyridine-3-carboxaldehyde (42 ml, 0.45 mol) at such a rate that the temperature of the reaction did not exceed 20° C. The solution was stirred with cooling for an additional two hours after the addition had been completed. To the above solution of N-(trimethylsilyl)pyridine-3-carboxaldimine was added a solution of benzylmagnesium chloride (0.5 m) in tetrahydrofuran (400 ml) and anhydrous ether (400 ml) at such a rate that the temperature of the reaction did not exceed 20° C. One hour after the addition was completed the cooling bath was removed and the reaction was stirred at ambient temperature overnight. The reaction was cooled in an ice-water bath and saturated ammonium chloride (1.5 L) was added. The mixture was stirred at ambient temperature for 1.5 hours. The phases were separated and the aqueous phase was extracted with ethyl acetate (800 ml). The combined organic phases were dried over MgSO$_4$. Removal of solvent gave 91.6 g of a reddish oil. The above oil was dissolved in 2N hydrochloric acid (600 ml) and ether (300 ml) and the two phase mixture was stirred at ambient temperature for 3 hours. The phases were separated and the aqueous phase was washed with ethyl acetate (500 ml). The aqueous phase was basified with 50% sodium hydroxide and extracted with chloroform (3×250 ml). The combined chloroform extracts were washed with saturated NaCl (200 ml) and dried over MgSO$_4$. Removal of solvent gave 81.2 g of reddish oil.

The above oil (54.0 g) was dissolved in ethyl acetate (50 ml) and methanol (70 ml) and acidified with HCl gas. A solid formed, on evaporation of a small amount of solvent under a stream of nitrogen, which was collected by filtration to give 16.46 g of 1-(3-pyridinyl)-2-phenylethylamine dihydrochloride of mp 270°–273° C. Recrystallization from methanol-ethanol and drying at 100° C. gave a sample of mp 272°–274° C.

Illustration 3

Preparation of 1-(4-Pyridinyl)-2-phenylethylamine dihydrochloride

By procedures essentially the same as those described in Illustration 1, and by substituting 1-(4-pyridinyl)-2-phenylethanone (Prasad, Al-Jallo and Al-Dulaimi, *J. Chem. Soc.* (c), (1969, 2134) for 1-(2-pyridinyl)-2-phenylethanone; the corresponding 1-(4-pyridinyl)-2-phenylethanone oxime, mp 133°–138° C. (cyclohexane-ether) and 1-(4-pyridinyl)-2-phenylethylamine, mp 267°–271° C. (ethanol) are prepared.

Illustration 4

Preparation of 1-Phenyl-2-(2-pyridinyl)ethylamine dihydrochloride

By procedures essentially the same as those described in Illustration 1, and by substituting 1-phenyl-2-(2-pyridinyl)ethanone (Cassity, Taylor, and Wolfe, *J. Org. Chem.*, 1978, 43, 2286) for 1-(2-pyridinyl)-2-phenylethanone; the corresponding 1-phenyl-2-(2-pyridinyl)ethanone oxime, mp 114°–117° C. (isopropanol-cyclohexane) and 1-phenyl-2-(2-pyridinyl)ethylamine, mp 219°–221° C. (ethylacetate-isopropanol-methanol) are obtained.

Illustration 5

Preparation of 1-Phenyl-2-(3-pyridinyl)ethylamine dihydrochloride

By procedures essentially the same as those described in Illustration 1, and by substituting, 1-phenyl-2-(3-pyridinyl)ethanone (Miller, Osuch, Goldberg and Levine, *J. Am. Chem. Soc.*, 1956, 78, 674) for 1-(2-pyridinyl)-2-phenylethanone the corresponding 1-phenyl-2-(3-pyridinyl)ethanone oxime, mp 152°–153° C. (isopropanol) and 1-phenyl-2-(3-pyridinyl)ethylamine dihydrochloride, mp 276°–278° C. (ethanol) are obtained.

illustration 6

Preparation of 1-Phenyl-2-(4-pyridinyl)ethylamine hydrochloride

By procedures essentially the same as those described in Illustration 1, and by substituting 1-phenyl-2-(4-pyridinyl)ethanone (Osuch and Levine, *J. Org. Chem.*, 1957, 22, 939) for 1-(2-pyridinyl)-2-phenylethanone; the corresponding 1-phenyl-2-(4-pyridinyl)ethanone oxime, mp 155°–157° C. (cyclohexane-isopropanol) and 1-phenyl-2-(4-pyridinyl)ethylamine dihydrochloride, mp 190°–192° C. (ethanol) are obtained.

Illustration 7

Preparation of N-Methyl-1-(3-pyridinyl)-2-phenylethylamine

Acylation of a primary amine with an alkyl chloroformate provides the N-carboalkoxy derivative which can be reduced with lithium aluminum hydride in ether solvents to provide the N-methyl secondary amine. For an example of this process see Horner and Skinner, *Can. J. Chem.*, 1966, 44, 315. Therefore, N-methyl-1-(3-pyridinyl)-2-phenylethylamine may be prepared by reaction of 1-(3-pyridinyl)-2-phenylethylamine with ethyl chloroformate in a two phase mixture of methylene chloride and aqueous sodium carbonate, followed by lithium aluminum hydride reduction in tetrahydrofuran of the intermediate N-carboethoxy-1-(3-pyridinyl)-2-phenylethylamine.

By procedures essentially the same as those described above, and by substituting 1-(2-pyridinyl)-2-phenylethylamine, 1-(4-pyridinyl)-2-phenylethylamine, 1-phenyl-2-(2-pyridinyl)ethylamine, 1-phenyl-2-(3-pyridinyl)ethylamine, or 1-phenyl-2-(4-pyridinyl)ethylamine for 1-(3-pyridinyl)-2-phenylethylamine; the corresponding N-methyl-1-(2-pyridinyl)-2-phenylethylamine, N-methyl-1-(4-pyridinyl)-2-phenylethylamine, N-methyl-1-phenyl-2-(2-pyridinyl)ethylamine, N-methyl-1-phenyl-2-(3-pyridinyl)ethylamine, or N-methyl-1-phenyl-2-(4-pyridinyl)ethylamine may be respectively prepared.

EXAMPLE 1

Preparation of 2-Amino-N-[1-(2-pyridinyl)-2-phenylethyl]acetamide dihydrochloride To a stirred solution of 1-(2-pyridinyl)-2-phenylethylamine (8.55 g, 0.043 mol) in chloroform (200 ml) was added N-CBZ-glycine (9.50 g, 0.045 mol) and then a solution of dicyclohexylcarbodiimide (9.79 g, 0.047 mol) in chloroform (80 ml) and the mixture stirred for 64 hours at ambient temperature. The mixture was filtered, the solvent evaporated, the residue dissolved in ethyl acetate (300 ml) and filtered again. The filtrate was washed with a pH 11 sodium carbonate solution, the aqueous phase back extracted with ethyl acetate (3×200 ml), and the organic phases combined, dried and evaporated to an oil, 19.6 g. This was dissolved in methanol (225 ml) and 10% HCl (50 ml) and hydrogenated at 40 psi in a Parr apparatus over 2.6 g of 10% Pd/C catalyst for 16 hours. The catalyst was removed by filtration, the solvent evaporated and the residue dissolved in water (300 ml) and chloroform (300 ml). The mixture was basified to pH 10 with 2N sodium carbonate, saturated with NaCl, shaken and separated. The aqueous layer was extracted with chloroform (3×250 ml) and ethyl acetate (2×250 ml), and the combined organic phases and dried and evaporated to a yellow oily solid, 10.3 g. This was dissolved in 100 ml of methanol and 100 ml isopropanol, acidified with HCl gas. The solid was collected by filtration, recrystallized from absolute ethanol (100 ml), and vacuum dried at 80° C. for 3 days to provide 6.13 g of 2-amino-N-[1-(2-pyridinyl)-2-phenylethyl]acetamide dihydrochloride, mp 148°–151° C.

EXAMPLE 2

Preparation of (2S)-2-Amino-N-[1-(2-pyridinyl)-2-phenylethyl]-propanamide dihydrochloride By procedures essentially the same as those described in Example 1, and by substituting N-CBZ-L-alanine for N-CBZ-glycine; the corresponding (2S)-2-amino-N-[1-(2-pyridinyl)-2-phenylethyl]propanamide dihydrochloride, mp 192°–195° C., is prepared.

EXAMPLE 3

Preparation of 2-(Methylamino)-N-[1-(2-pyridinyl)-2-phenylethyl]acetamide dihydrochloride To a stirred solution of 1-(2-pyridinyl)-2-phenylehtylamine.2HCl (15.0 g, 0.055 mol) in chloroform (175 ml) at 0° under nitrogen, was added triethylamine (33.39 g, 0.33 mol) and then dropwise a solution of chloroacetyl chloride in 20 ml of chloroform and the mixture was allowed to warm to ambient temperature and stirred for 18 hours. The reaction was not quite complete by TLC, so an additional 2 g of chloroacetyl chloride and 25 ml of triethylamine was added and stirring continued for 60 hours. The mixture was poured into 300 ml of water and 300 ml of chloroform, the solution basified to pH 9 with 1N sodium bicarbonate, shaken and the layers separated. The aqueous phase was extracted with 3×250 ml of chloroform and 2×250 ml of ethyl acetate. The organic layers were combined, washed with brine, dried and evaporated to a brown oil, 17.8 g.

This oil (17.8 g, 0.065 mol) was dissolved in chloroform (233 ml) and methanol (583 ml), cooled to 0° C. and treated with monomethylamine (58 ml) and stirred for 20 hours. An additional 40 ml of monomethylamine was added and the mixture stirred at ca 20° C. for 20 hours. The reaction was complete by TLC analysis. The solvent was evaporated and the residue was dissolved in 300 ml of water and 200 ml of chloroform. The mixture was basified with 25% NaOH to pH 11, shaken, and the layers separated. The aqueous layer was extracted with chloroform (2×350 ml) and the combined organic layers washed with water, decolorized with charcoal, dried and evaporated to a light brown oil, 12.4 g. This oil was purified by chromatography on a Prep 500 HPLC on silica gel, eluting with 2% methanol/chloroform. Pure fractions were combined and evaporated to give 7.3 g of a yellow oil. This oil was dissolved in 100 ml ethyl acetate and acidified with HCl gas. The resulting solid salt was collected by filtration, recrystallized from isopropanol/methanol (100 ml), and vacuum dried to give 2-(methylamino)-N-[1-(2-pyridinyl)-2-phenylethyl]acetamide dihydrochloride as a white solid, mp 215°-221° C.

By procedures essentially the same as those described above, and by substituting cyclopropylamine for monomethylamine; the corresponding 2-(cyclopropylamino)-N-[1-(2-pyridinyl)-2-phenylethyl]acetamide may be prepared.

EXAMPLE 4

Preparation of 2-(Butylamino)-N-[1-(2-pyridinyl)-2-phenylethyl]acetamide dihydrochloride By procedures essentially the same as those described in Example 3, and by substituting n-butylamine for monomethylamine the corresponding 2-(butylamino)-N-[1-(2-pyridinyl)-2-phenylethyl]acetamide dihydrochloride, mp 250°-252° C., is prepared.

EXAMPLE 5

Preparation of 2-Amino-N-[1-(3-pyridinyl)-2-phenylethyl]acetamide dihydrochloride By procedures essentially the same as those described in Example 1, and by substituting 1-(3-pyridinyl)-2-phenylethylamine for 1-(2-pyridinyl)-2-phenylethylamine; the corresponding 2-amino-N-[1-(3-pyridinyl)-2-phenylethyl]acetamide dihydrochloride, mp 169°-173° C., is prepared.

EXAMPLE 6

Preparation of 2-Amino-N-[1-(4-pyridinyl)-2-phenylethyl]acetamide dihydrochloride hydrate By procedures essentially the same as those descrbied in Example 1, and by substituting 1-(4-pyridinyl)-2-phenylethylamine for 1-(2-pyridinyl)-2-phenylethylamine; the corresponding 2-amino-N-[1-(4-pyridinyl)-2-phenylethyl]acetamide dihydrochloride hydrate, mp 159°-169° C., is prepared.

EXAMPLE 7

Preparation of 2-(Butylamino)-N-[1-(4-pyridinyl)-2-phenylethyl]acetamide maleate By procedures essentially the same as those described in Example 3; and by substituting 1-(4-pyridinyl)-2-phenylethylamine for 1-(2-pyridinyl)-2-phenylethylamine and n-butylamine for methylamine and maleic acid for hydrogen chloride respectively; the corresponding 2-(butylamino)-N-[1-(4-pyridinyl)-2-phenylethyl]acetamide maleate, mp 145°-146° C., is prepared.

EXAMPLE 8

Preparation of 2-Amino-N-[1-phenyl-2-(2-pyridinyl)ethyl]acetamide

By procedures essentially the same as those described in Example 1, and substituting 1-phenyl-2-(2-pyridinyl)ethylamine for 1-(2-pyridinyl)-2-phenylethylamine; the corresponding 2-amino-N-[1-phenyl-2-(2-pyridinyl)ethyl]acetamide, mp 75°-77° C., is prepared.

EXAMPLE 9

Preparation of 2-Amino-N-[1-phenyl-2-(3-pyridinyl)ethyl]acetamide

By procedures essentially the same as those described in Example 1, and by substituting 1-phenyl-2-(3-pyridinyl)ethylamine for 1-(2-pyridinyl)-2-phenylethylamine; the corresponding 2-amino-N-[1-phenyl-2-(3-pyridinyl)ethyl]acetamide, mp 93.5°-94.5° C., is obtained.

EXAMPLE 10

Preparation of 2-Amino-N-[1-phenyl-2-(4-pyridinyl)ethyl]acetamide

By procedures essentially the same as those described in Example 1, and by substituting 1-phenyl-2-(4-pyridinyl)ethylamine for 1-(2-pyridinyl)-2-phenylethylamine; the corresponding 2-amino-N-[1-phenyl-2-(4-pyridinyl)ethyl]acetamide, mp 145°-147° C., is obtained.

EXAMPLE 11

Preparation of 2-(Dialkylamino)-N-[1-(2-pyridinyl)-2-phenylethyl]acetamides

By procedures essentially the same as those described in Example 3, and by substituting dimethylamine or diethylamine for monomethylamine; the corresponding 2-(dimethylamino)-N-[1-(2-pyridinyl-2-phenylethyl]acetamide or 2-(diethylamino)-N-[1-(2-pyridinyl)-2-phenylethyl]acetamide may be respectively prepared.

EXAMPLE 12

Preparation of 2-(Azacyclo)-N-[1-(2-pyridinyl)-2-phenylethyl]acetamides

By procedures essentially the same as those described in Example 3, and by substituting pyrrolidine, piperidine or morpholine for monomethylamine; the corresponding 2-(1-pyrrolidinyl)-N-[1-(2-pyridinyl)-2-phenylethyl]acetamide, 2-(1-piperidinyl)-N-[1-(2-pyridinyl)-2-phenylethyl]acetamide or 2-(4-morpholinyl)-N-[1-(2-pyridinyl)-2-phenylethyl]acetamide may be respectively prepared.

EXAMPLE 13

Preparation of 2-Amino-N-methyl-N-[1-(3-pyridinyl)-2-phenylethyl]acetamide

By procedures essentially the same as those described in Example 1, and by substituting N-methyl-1-(3- pyridinyl)-2-phenylethylamine for 1-(2-pyridinyl)-2-phenylethylamine the corresponding 2-amino-N-methyl-N-[1-(3-pyridinyl)-2-phenylethyl]acetamide may be prepared.

What is claimed:

1. The compound

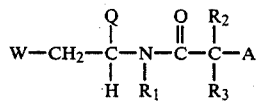

wherein $R_1$, $R_2$ and $R_3$ are independently selected from hydrogen or methyl; A is amino, $C_1$–$C_4$ monoalkylamino, $C_2$–$C_8$ dialkylamino, or cyclopropylamino; and where W and Q are independently selected from 2-pyridinyl, 3-pyridinyl or 4-pyridinyl or phenyl provided W and Q are not both phenyl.

2. 2-amino-N-[1-(2-pyridinyl)-2-phenylethyl]acetamide dihydrochloride.

3. (2S)-2-amino-N-[1-(2-pyridinyl)-2-phenylethyl]propanamide dihydrochloride.

4. 2-(methylamino)-N-[1-(2-pyridinyl)-2-phenylethyl]acetamide dihydrochloride.

5. 2-(butylamino)-N-[1-(2-pyridinyl)-2-phenylethyl]acetamide dihydrochloride.

6. 2-amino-N-[1-(3-pyridinyl)-2-phenylethyl]acetamide dihydrochloride.

7. 2-amino-N-[1-(4-pyridinyl)-2-phenylethyl]acetamide dihydrochloride hydrate.

8. 2-(butylamino)-N-[1-(4-pyridinyl)-2-phenylethyl]acetamide maleate.

9. 2-amino-N-[1-phenyl-2-(2-pyridinyl)ethyl]acetamide.

10. 2-amino-N-[1-phenyl-2-(3-pyridinyl)ethyl]acetamide.

11. 2-amino-N-[1-phenyl-2-(4-pyridinyl)ethyl]acetamide.

* * * * *